US012586664B2

(12) United States Patent (10) Patent No.: US 12,586,664 B2
Lee et al. (45) Date of Patent: Mar. 24, 2026

(54) MATERIAL SYNTHESIS APPARATUS AND METHOD OF OPERATING THE SAME

(71) Applicant: SAMSUNG ELECTRONICS CO., LTD., Suwon-si (KR)

(72) Inventors: Dongseon Lee, Suwon-si (KR); Taesin Ha, Seongnam-si (KR); Younsuk Choi, Seongnam-si (KR); Jeonghun Kim, Suwon-si (KR); Wonseok Oh, Suwon-si (KR); Hyunjeong Jeon, Suwon-si (KR); Byungkwon Choi, Seongnam-si (KR); Youngchun Kwon, Yongin-si (KR); Hyukju Kwon, Uiwang-si (KR); Gahee Kim, Yongin-si (KR); Bosung Kim, Suwon-si (KR); Eunji Kim, Suwon-si (KR); Minsik Min, Suwon-si (KR); Minsik Park, Hwaseong-si (KR); Youngjin Park, Seoul (KR); Jinwoo Park, Suwon-si (KR); Hyungtae Seo, Suwon-si (KR); Sangyoon Lee, Yongin-si (KR); Jaejun Chang, Gwacheon-si (KR); Junwon Jang, Seoul (KR); Aram Jeon, Seoul (KR); Yongsik Jung, Seoul (KR); Joonkee Cho, Yongin-si (KR); Wonje Choi, Suwon-si (KR); Hyundo Choi, Yongin-si (KR); Dal Heo, Yongin-si (KR); Wooram Hong, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1190 days.

(21) Appl. No.: 17/507,401

(22) Filed: Oct. 21, 2021

(65) Prior Publication Data

US 2022/0319642 A1 Oct. 6, 2022

(30) Foreign Application Priority Data

Mar. 30, 2021 (KR) ........................ 10-2021-0041357

(51) Int. Cl.
*G16C 20/10* (2019.01)
*G05B 13/02* (2006.01)
(Continued)

(52) U.S. Cl.
CPC ......... *G16C 20/10* (2019.02); *G05B 13/0265* (2013.01); *G05B 13/048* (2013.01); *G16C 20/70* (2019.02)

(58) Field of Classification Search
CPC ...... G16C 20/70; G16C 20/10; G05B 13/048; G05B 13/0265
See application file for complete search history.

(56) References Cited

U.S. PATENT DOCUMENTS 5,463,564 A 10/1995 Agrafiotis et al.
6,044,212 A 3/2000 Flavin et al.
(Continued)

FOREIGN PATENT DOCUMENTS

JP 2008-150337 A 7/2008
JP 5099511 B2 12/2012

OTHER PUBLICATIONS

Sebastian Steiner et al., "Organic synthesis in a modular robotic system driven by a chemical programming language", Science, 363, Jan. 2019, 10 pages total.
(Continued)

*Primary Examiner* — Shogo Sasaki
(74) *Attorney, Agent, or Firm* — Sughrue Mion, PLLC

(57) ABSTRACT

A material synthesis apparatus includes: at least one device configured to synthesize a material; a user interface configured to obtain information on a target product; and a
(Continued)

processor, wherein the processor is configured to: determine synthesis conditions for preparing the target product using a pretrained synthesis prediction model; calculate a first synthesis method for preparing the target product based on the synthesis conditions; and control the at least one device based on the first synthesis method.

7 Claims, 10 Drawing Sheets

(51) Int. Cl.
    *G05B 13/04*        (2006.01)
    *G16C 20/70*      (2019.01)

(56)              References Cited

U.S. PATENT DOCUMENTS

| | | | |
|---|---|---|---|
| 2011/0106794 A1 | 5/2011 | Hori et al. | |
| 2018/0196913 A1 | 7/2018 | Yoshikawa et al. | |
| 2020/0379442 A1* | 12/2020 | Chan | B01J 19/0033 |
| 2022/0172802 A1* | 6/2022 | Konstantinov | G16C 20/70 |
| 2022/0397886 A1* | 12/2022 | Hong | G16C 20/10 |

OTHER PUBLICATIONS

Connor W. Coley et al., "A robotic platform for flow synthesis of organic compounds informed by AI planning", Science, 365, Aug. 2019, 11 pages total.

* cited by examiner

FIG. 4

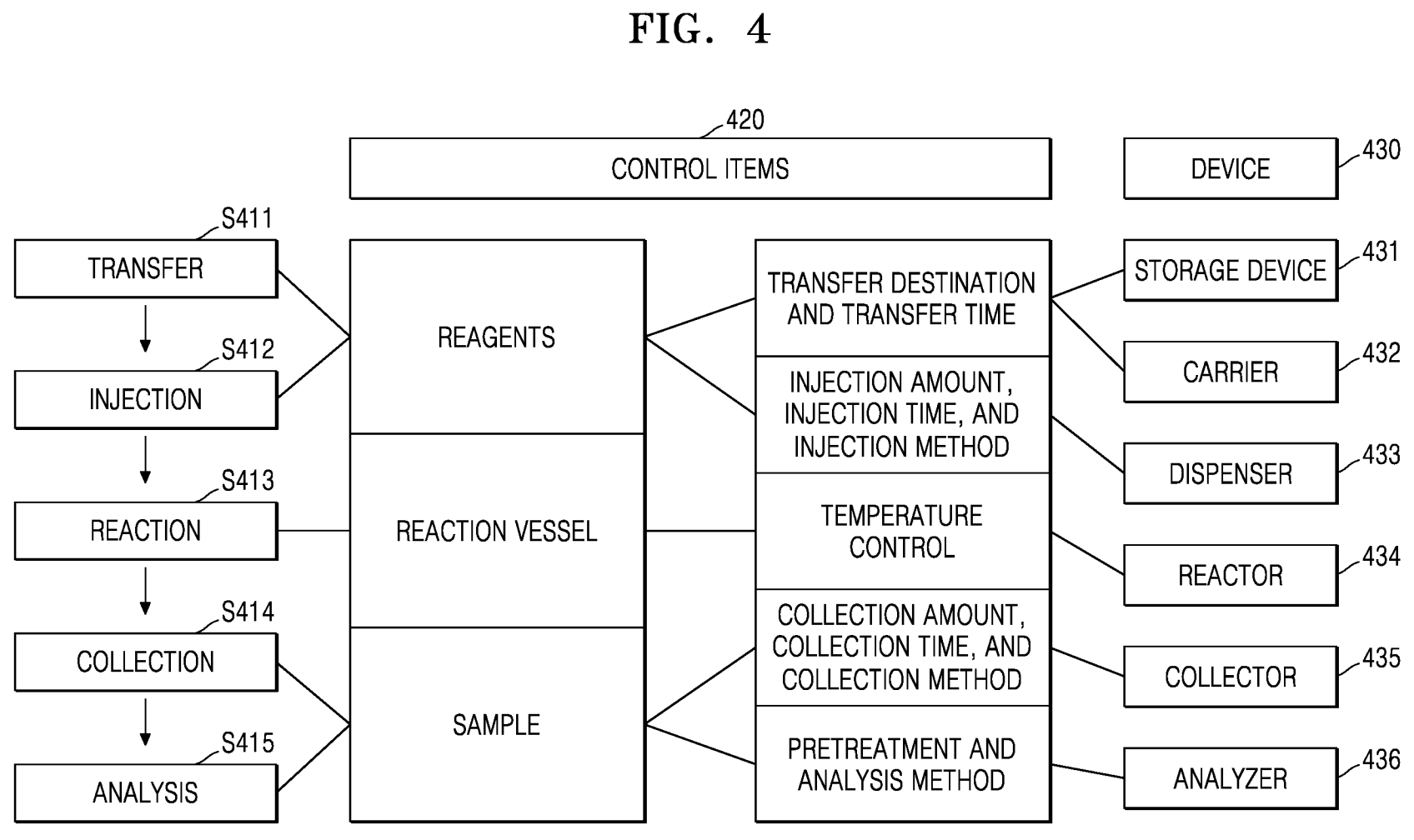

430 DEVICE

431 STORAGE DEVICE
432 CARRIER
433 DISPENSER
434 REACTOR
435 COLLECTOR
436 ANALYZER

420 CONTROL ITEMS

TRANSFER DESTINATION AND TRANSFER TIME

INJECTION AMOUNT, INJECTION TIME, AND INJECTION METHOD

TEMPERATURE CONTROL

COLLECTION AMOUNT, COLLECTION TIME, AND COLLECTION METHOD

PRETREATMENT AND ANALYSIS METHOD

REAGENTS

REACTION VESSEL

SAMPLE

S411 TRANSFER

S412 INJECTION

S413 REACTION

S414 COLLECTION

S415 ANALYSIS

FIG. 5
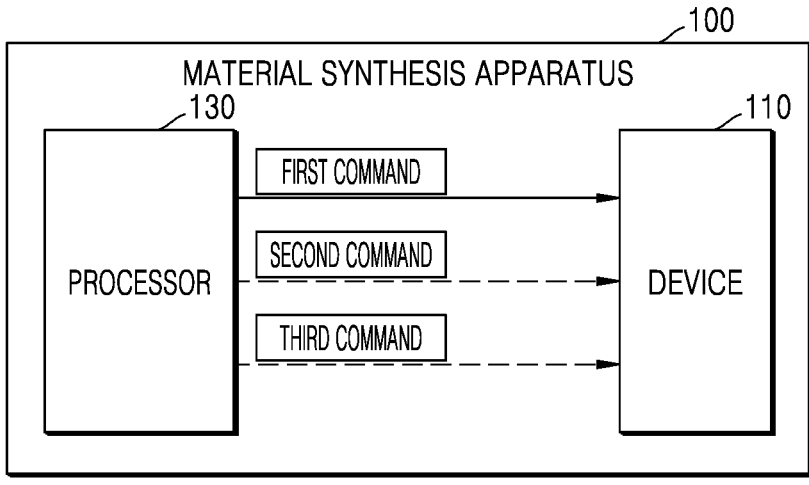
FIRST TIME
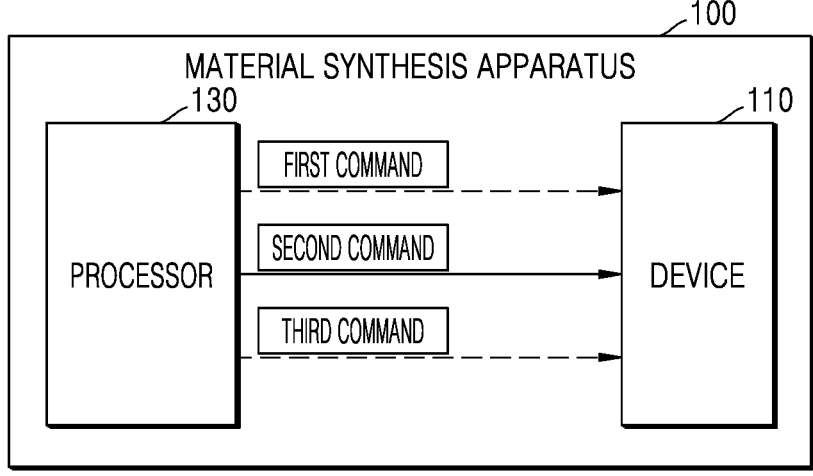
SECOND TIME
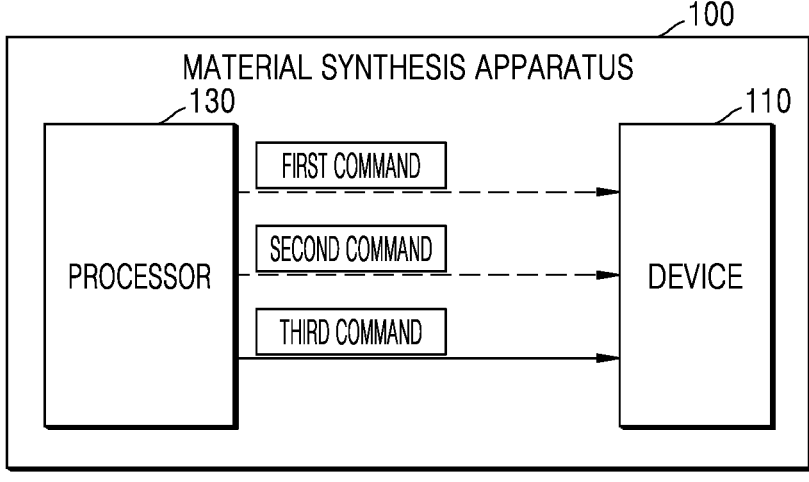
THIRD TIME

MATERIAL SYNTHESIS APPARATUS AND METHOD OF OPERATING THE SAME

CROSS-REFERENCE TO RELATED APPLICATION

This application is based on and claims priority under 35 U.S.C. § 119 from Korean Patent Application No. 10-2021-0041357, filed on Mar. 30, 2021, in the Korean Intellectual Property Office, the disclosure of which is incorporated by reference herein in its entirety.

BACKGROUND

1. Field

The disclosure relates to a material synthesis apparatus and a method of operating the material synthesis apparatus.

2. Description of the Related Art

Techniques of obtaining information on a target product, calculating a synthesis method for preparing the target product based on the obtained information, and controlling a device based on the calculated synthesis method are widely used for research purposes as well as industrial purposes.

Material synthesis techniques of the related art require the intervention of a user during at least some of the material synthesis processes. Therefore, automation techniques are needed for automatically performing the entire material synthesis processes without the user intervention.

SUMMARY

Provided are material synthesis apparatuses and methods of operating the material synthesis apparatuses. Provided are non-transitory computer-readable recording media having recorded thereon programs for executing the methods on computers. Technical aspects of the disclosure are not limited thereto, and other technical aspects of the disclosure may be inferred from the following embodiments.

Additional aspects will be set forth in part in the description which follows and, in part, will be apparent from the description, or may be learned by practice of the presented embodiments of the disclosure.

According to an aspect of the disclosure, there is provided a material synthesis apparatus including: at least one device configured to synthesize a material; a user interface configured to obtain information on a target product; and a processor is configured to: determine one or more synthesis conditions for preparing the target product using a pretrained synthesis prediction model; determine a first synthesis method for preparing the target product based on the one or more synthesis conditions; and control the at least one device based on the first synthesis method.

The user interface is further configured to obtain a target synthesis result regarding the target product, wherein the processor is further configured to: obtain a first synthesis result based on the first synthesis method; determine, based on a result of a comparison between the target synthesis result and the first synthesis result, whether to determine a second synthesis method which is different from the first synthesis method; and control the at least one device based on the second synthesis method based on the determination to determine the second synthesis method.

The processor is further configured to: calculate a value by subtracting the target synthesis result from the first synthesis result, and determine the second synthesis method based on whether the value satisfies a specific condition.

The target synthesis result includes at least one of a target synthesis yield, a target synthesis amount, or a target synthesis time of the target product.

The material synthesis apparatus may further include a memory configured to store the pretrained synthesis prediction model, wherein the processor is further configured to: determine a synthesis route for synthesizing the target product by using the pretrained synthesis prediction model; determine the one or more synthesis conditions corresponding to the synthesis route; determine the first synthesis method based on the determined synthesis route and the determined one or more synthesis conditions; and determine the second synthesis method by changing, based on the first synthesis result, at least one of the determined synthesis route or the determined one or more synthesis conditions.

The information on the target product includes structure information on the target product.

The processor is further configured to transmit a combination of commands for synthesizing the target product to the at least one device.

The at least one device is further configured to sequentially perform the commands included in the combination of commands.

The material synthesis apparatus further including a communication interface configured to receive a target synthesis result regarding the target product from an external device.

According to another aspect of the disclosure, there is a method of operating a material synthesis apparatus, the method including: obtaining information on a target product through an user interface; determining one or more synthesis conditions for preparing a target product using a pretrained synthesis prediction model; determining a first synthesis method for preparing the target product based on the one or more synthesis conditions; and controlling at least one device based on the first synthesis method.

The method further including: obtaining a target synthesis result regarding the target product through the user interface.

The method further including: obtaining a first synthesis result based on the first synthesis method; determining, based on a result of a comparison between the target synthesis result and the first synthesis result, whether to determine a second synthesis method which is different from the first synthesis method; and controlling the at least one device based on the second synthesis method, based on the determination to determine the second synthesis method.

The determining of whether to calculate the second synthesis method includes: calculating a value by subtracting the target synthesis result from the first synthesis result; and determining, based on whether the value satisfies a specific condition, the second synthesis method.

The target synthesis result includes at least one of a target synthesis yield, a target synthesis amount, or a target synthesis time of the target product.

The calculating of the first synthesis method includes: determining a synthesis route for synthesizing the target product by using the pretrained synthesis prediction model; determining the one or more synthesis conditions corresponding to the synthesis route; and determining the first synthesis method based on the determined synthesis route and the determined one or more synthesis conditions, wherein the determining of the second synthesis method includes changing, based on the first synthesis result, at least one of the determined synthesis route or the determined synthesis conditions.

The information on the target product includes structure information on the target product.

The controlling of the at least one device includes transmitting a combination of commands for synthesizing the target product to the at least one device.

The controlling of the at least one device includes sequentially performing the commands included in the combination of commands.

According to another aspect of the disclosure, there is provided a non-transitory computer-readable recording medium having recorded thereon a program for executing a method including: obtaining information on a target product through an user interface; determining one or more synthesis conditions for preparing a target product using a pretrained synthesis prediction model; determining a first synthesis method for preparing the target product based on the one or more synthesis conditions; and controlling at least one device based on the first synthesis method.

The non-transitory computer-readable recording medium further including: obtaining a first synthesis result based on the first synthesis method; determining, based on a result of a comparison between a target synthesis result and the first synthesis result, whether to determine a second synthesis method which is different from the first synthesis method; and controlling the at least one device based on the second synthesis method, based on the determination to determine the second synthesis method.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 4 is a diagram illustrating a method of controlling at least one device by using a processor according to an example embodiment;

FIGS. 5 and 6 are diagrams illustrating a method of transmitting commands to the at least one device from the processor according to an example embodiment;

DETAILED DESCRIPTION

Figure 1:
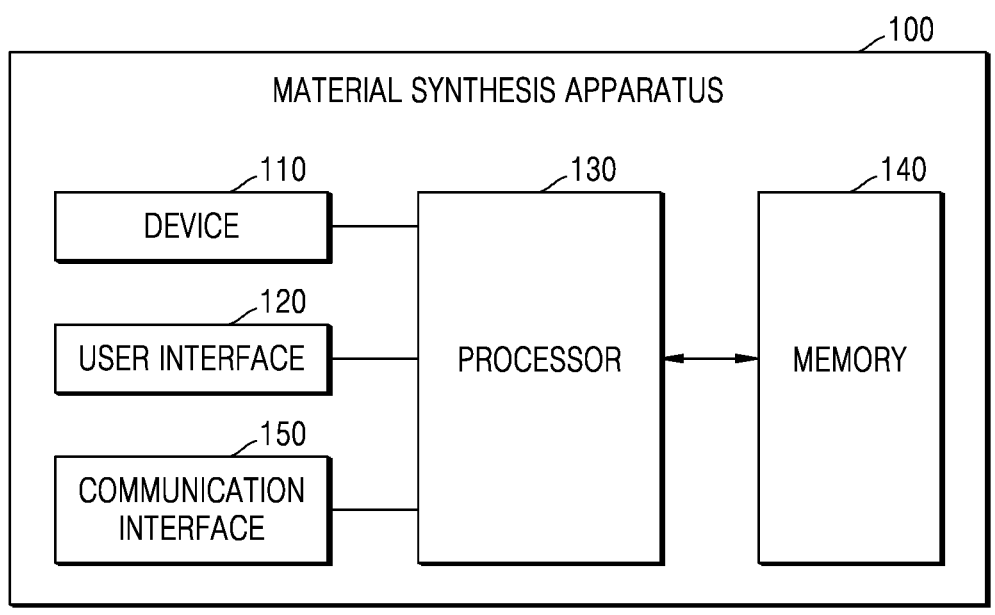
FIG. 1 is a block diagram illustrating a configuration of a material synthesis apparatus according to an example embodiment.

Reference will now be made in detail to embodiments, examples of which are illustrated in the accompanying drawings, wherein like reference numerals refer to like elements throughout. In this regard, the example embodiments may have different forms and should not be construed as being limited to the descriptions set forth herein. Accordingly, the example embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Phrases such as "in some embodiments" or "in one embodiment" appearing in various parts of the disclosure should not be construed as always referring to the same embodiment(s).

The terms used in the disclosure are general terms currently widely used in the art in consideration of functions regarding the disclosure, but the terms may vary according to the intention of those of ordinary skill in the art, precedents, or new technology in the art. Also, some terms may be arbitrarily selected by the applicant, and in this case, the meaning of the selected terms will be described in the detailed description of the disclosure. Thus, the terms used herein should not be construed based on only the names of the terms but should be construed based on the meaning of the terms together with the description throughout the disclosure.

The terms of a singular form may include plural forms unless otherwise mentioned. It will be further understood that the terms "comprises" and/or "comprising" used herein specify the presence of stated features or elements, but do not preclude the presence or addition of one or more other features or elements.

In the following descriptions of the embodiments, expressions or terms such as "constituted by," "formed by," "include," "comprise," "including," and "comprising" should not be construed as always including all specified elements, processes, or operations, but may be construed as not including some of the specified elements, processes, or operations, or further including other elements, processes, or operations.

It will be understood that although terms including ordinal numbers such as "first" and "second" may be used herein to describe various elements, these elements should not be limited by these terms. These terms are only used to distinguish one element from element.

Some embodiments of the disclosure may be implemented as functional blocks and various processing operations. Some or all of the functional blocks may be implemented with various hardware and/or software configurations executing specific functions. For example, the functional blocks of the disclosure may be implemented with one or more microprocessors or circuit configurations having given functions. In addition, the functional blocks of the disclosure may be implemented with various programming or streaming languages. The functional blocks may be implemented by algorithms executed on one or more processors. In some example embodiment, the functional blocks may be referred to as "unit(s)" or "module(s)". Also, example embodiments of the disclosure may employ conversional arts to establish an electronic environment, process signals and/or process data. Terms such as "mechanism," "element," "means," and "configuration" may be widely used and are not limited to mechanical and physical configurations.

Furthermore, line connections or connection members between elements depicted in the drawings represent functional connections and/or physical or circuit connections by way of example. In actual applications, connections between elements may be implemented with various additional functional connections, physical connections or circuit connections.

The following descriptions of the embodiments should not be construed as limiting the scope of the disclosure, and modifications or changes that could be easily made from the embodiments by those of ordinary skill in the art should be construed as being included in the scope of the disclosure. Hereinafter, example embodiments will be described with reference to the accompanying drawings.

FIG. 1 is a block diagram illustrating a configuration of a material synthesis apparatus 100 according to an example embodiment.

The material synthesis apparatus 100 corresponds to any material synthesis apparatus and is not limited to a particular material synthesis apparatus. For example, the material synthesis apparatus 100 may correspond to an apparatus used for synthesizing a material in a small amount for research purposes as well as an apparatus used for industrially producing a large amount of a chemical product. In addition, the term "material" may refer to a product synthesized by a chemical method, and examples of the material may include, but are not limited to, a single molecule, a polymer, and an organometallic compound.

Referring to FIG. 1, the material synthesis apparatus 100 may include at least one device 110, a user interface 120, a processor 130, a memory 140, and a communication interface 150. Here, FIG. 1 illustrates only elements of the material synthesis apparatus 100 which are related to explanation of the example embodiment. Therefore, it is apparent to those of ordinary skill in the art that the material synthesis apparatus 100 may further include, other elements, such as general-purpose elements, in addition to the elements shown in FIG. 1.

Furthermore, according to another example embodiment, when an objective of the disclosure is achievable using only some of the elements shown in FIG. 1, an apparatus including only some of the elements shown in FIG. 1 may correspond to the material synthesis apparatus 100. For example, the material synthesis apparatus 100 may include only the user interface 120, the processor 130, the memory 140, and the communication interface 150, and the at least one device 110 may be provided outside the material synthesis apparatus 100.

The at least one device 110 may refer to any device used to synthesize a material for producing a target product. For example, the at least one device 110 may include, but is not limited to, at least one selected from the group including a storage device 431, a carrier 432, a dispenser 433, a reactor 434, a collector 435, and an analyzer 436 (refer to FIG. 4).

The storage device 431 may be used to store reagents in a particular environment, and examples of the storage device 431 may include a refrigerator, a hot storage cabinet, and a vacuum chamber. The particular environment may be a predetermined environment. The carrier 432 may be used to move reagents or tools to a specific location, and examples of the carrier 432 may include a transfer robot, a lift, and a conveyor belt.

The reactor 434 may include a reaction vessel in which a chemical reaction may occur, and may also include a heater or a pump to control the temperature or gas composition in the reaction vessel. The dispenser 433 may be used to inject a reagent into the reaction vessel, and the collector 435 may be used to collect a sample from the reaction vessel. Examples of the dispenser 433 and the collector 435 may include syringes, pipettes, burettes, and droppers. The analyzer 436 may be used to analyze a sample, and, if necessary, the analyzer 436 may perform a pretreatment on a sample before analyzing the sample. Examples of the analyzer 436 may include a scale, a chromatographer, and a spectrometer.

Embodiments of the disclosure are not limited to the above-mentioned examples of the storage device 431, the carrier 432, the dispenser 433, the reactor 434, the collector 435, and the analyzer 436.

The user interface 120 may refer to a device used to input information on a target product. Examples of the user interface 120 may include a key pad, a dome switch, a touch pad (of a capacitive touch type, a resistive overlay type, an infrared beam type, a surface acoustic wave type, an integral strain gauge type, a piezoelectric type, or the like), a jog wheel, a jog switch, etc., but the user interface 120 is not limited thereto.

According to an example embodiment, information on a target product may include structure information on the target product. The structure information may refer to an index value used to express the structure of a material such as a structural feature value indicating whether a specific partial structure is included. For example, the structural feature value may be an extended connectivity fingerprint (ECFP).

In addition, the material synthesis apparatus 100 may further obtain a target synthesis result regarding a target product by using the user interface 120. The target synthesis result may indicate that an index related to the synthesis of the target product may be expressed as an arbitrary quantitative value. Examples of the target synthesis result may include, but are not limited to, a target synthesis yield, a target synthesis amount, and a target synthesis time.

The user interface 120 may include a display, and a user may monitor results of synthesis through the display. Furthermore, in some example embodiments, a user may manually control the at least one device 110 through the user interface 120.

The memory 140 is hardware configured to store various types of data about processes in the material synthesis apparatus 100, and for example, the memory 140 may store data processed by the material synthesis apparatus 100 and data to be processed by the material synthesis apparatus 100. In addition, the memory 140 may store applications, drivers, etc. to be executed on the material synthesis apparatus 100.

Examples of the memory 140 may include random access memory (RAM), such as dynamic random access memory (DRAM) and static random access memory (SRAM), read-only memory (ROM), electrically erasable programmable read-only memory (EEPROM), a CD-ROM, a Blu-ray or other optical disk storage, hard disk drives (HDDs), solid state drives (SSDs), and flash memory, and the memory 140 may include an external storage device that is accessible by the material synthesis apparatus 100.

In addition, a pretrained synthesis prediction model may be stored in the memory 140. The synthesis prediction model may be generated by the processor 130 based on a database such as Reaxys or SciFinder. For example, the processor 130 may generate the synthesis prediction model using a deep neural network (DNN), a recurrent neural network (RNN), a conditional variational autoencoder (CVAE), or the like.

The synthesis prediction model may store at least one selected from the group including structure information on reactants, structure information on products, and synthesis yields, amounts, and times which are predicted based on synthesis routes and synthesis conditions. The processor 130 may update the synthesis prediction model by receiving at least one selected from the group including a predicted synthesis yield, a predicted synthesis amount, and a predicted synthesis time from the synthesis prediction model, or by receiving results of synthesis as feedback.

For example, the processor 130 may update the synthesis prediction model to increase the synthesis yield or synthesis amount of a product. Alternatively, the processor 130 may update the synthesis prediction model to decrease a synthesis time of a product. The synthesis prediction model may be optimized through updates such that a user may obtain desired results of synthesis using the synthesis prediction model.

The memory 140 may store information for optimizing synthesis. For example, the information for optimizing synthesis may include information on reagents and information on the at least one device 110. In addition, the information for optimizing synthesis may further include structure information on reactants, structure information on products, and results of synthesis dependent on synthesis routes and synthesis conditions. For example, the results of synthesis may include results of the current synthesis and results of previous synthesis as well. The processor 130 may update the synthesis prediction model by receiving, from the memory 140, information for optimizing synthesis.

The communication interface 150 may refer to a device for transmitting and receiving various types of data. The material synthesis apparatus 100 may communicate with an external device through the communication interface 150. The communication interface 150 may include a short-range wireless communication interface, a mobile communication interface, or the like. The short-range wireless communication interface may include, but is not limited to, a Bluetooth communication interface, a Bluetooth Low Energy (BLE) communication interface, a near field communication interface, a WLAN (Wi-Fi) communication interface, a Zigbee communication interface, an infrared (Infrared Data Association (IrDA)) communication interface, a Wi-Fi Direct (WFD) communication interface, a ultrawideband (UWB) communication interface, an Ant+ communication interface, or the like.

The material synthesis apparatus 100 may communicate with an external device to receive target synthesis results regarding a target product from the external device, such that a user may operate the material synthesis apparatus 100 to prepare the target product without restriction of time and place. In addition, an external device may provide target synthesis results regarding target products to a plurality of material synthesis apparatuses 100 such that a user may simultaneously operate the plurality of material synthesis apparatuses 100 to prepare a target product in a large amount or various target products at the same time.

The processor 130 may control all functions for operating the material synthesis apparatus 100. For example, the processor 130 may generally control the material synthesis apparatus 100 by executing programs stored in the memory 140 of the material synthesis apparatus 100. As a non-limiting example of the processor 130, a central processing unit (CPU), a graphics processing unit (GPU), an application processor (AP), or the like may be provided in the material synthesis apparatus 100.

The processor 130 may use the synthesis prediction model stored in the memory 140 to calculate a synthesis method for preparing a target product. The synthesis prediction model may be at least one selected from the group including DNNs, RNNs, and CVAEs, but is not limited thereto.

The synthesis method may include a synthesis route and synthesis conditions. The synthesis route may refer to a chemical reaction for preparing a product using reactants. For example, when a biaryl compound is prepared as a produce by using an organo-boronic compound and a halogenated aryl compound as reactants, the synthesis route may be a Suzuki-Miyaura reaction. A plurality of synthesis routes may exist according to structure information on reactants and structure information on a product.

The synthesis conditions may refer to various conditions of a chemical reaction which are set for preparing a product by using reactants, and at least one synthesis condition may be set for one synthesis route. For example, the synthesis conditions may include at least one selected from the group including a catalyst, a base, a solvent, a reagent, a temperature, and a reaction time, but is not limited thereto.

A test data set for training the synthesis prediction model may include structure information on reactants and structure information on products, and may further include synthesis routes and synthesis conditions included in the synthesis method. The processor 130 may train the synthesis prediction model using the test data set.

The processor 130 may predict synthesis results by using the pretrained synthesis prediction model according to the structure information on reactants, the structure information on products, the synthesis routes, and the synthesis conditions. For example, the predicted synthesis results may include at least one selected from the group including a predicted synthesis yield, a predicted synthesis amount, and a predicted synthesis time, but are not limited thereto. According to an example embodiment, the processor 130 may additionally train the synthesis prediction model by using actual results of synthesis corresponding to the synthesis routes and the synthesis conditions. For example, the actual results of synthesis may include at least one selected from the group including an actual synthesis yield, an actual synthesis amount, and an actual synthesis time, but are not limited thereto.

The processor 130 may determine a synthesis route for synthesizing a target product by using the pretrained synthesis prediction model. The processor 130 may determine synthesis conditions for the determined synthesis route by using the pretrained synthesis prediction model, and may calculate a first synthesis method based on the determined synthesis route and the synthesis conditions.

In some example embodiments, the processor 130 may obtain a first synthesis result from a target product prepared using the first synthesis method. The first synthesis result may refer to an arbitrary quantitative value of an index related to the synthesis of the target product prepared using the first synthesis method. Examples of the first synthesis result may include, but are not limited to, the synthesis yield, synthesis amount, and synthesis time of the target product prepared using the first synthesis method.

Based on results of comparison between a target synthesis result and the first synthesis result, the processor 130 may determine whether to calculate a second synthesis method which is different from the first synthesis method. For example, the processor 130 may calculate a value by subtracting the target synthesis result from the first synthesis result, and based on whether the value obtained by subtracting the target synthesis result from the first synthesis result satisfies a specific condition, the processor 130 may determine whether to calculate the second synthesis method. The specific condition may be a preset condition.

The target synthesis result may include a quantitative index related to a synthesis yield, a synthesis amount, or a synthesis time. When the quantitative index of the target synthesis result is a synthesis yield, the preset condition may be "0% or more." For example, when a target synthesis yield is 80% and the synthesis yield (first synthesis result) of the target product is 85%, the first synthesis result—the target synthesis result 0%, and thus, the processor 130 may not calculate the second synthesis method. However, when the target synthesis yield is 80% and the synthesis yield (first synthesis result) of the target product is 75%, the first synthesis result—the target synthesis result<0%, and thus, the processor 130 may calculate the second synthesis method.

When the quantitative index of the target synthesis result is a synthesis amount, the preset condition may be "10 g or more." For example, when a target synthesis amount is 100 g and the synthesis amount (first synthesis result) of the target product is 120 g, the first synthesis result—the target synthesis result 10 g, and thus, the processor 130 may not calculate the second synthesis method. However, when the target synthesis yield is 100 g and the synthesis yield (first synthesis result) of the target product is 85 g, the first synthesis result—the target synthesis result<10 g, and thus, the processor 130 may calculate the second synthesis method.

When the quantitative index for the target synthesis results is a synthesis time, the preset condition may be "1 hour or less." For example, when a target synthesis time is 12 hours and the synthesis time (first synthesis result) of the target product is 8 hours, the first synthesis result—the target synthesis result 1 hour, and thus, the processor 130 may not calculate the composition method. However, when the target synthesis time is 12 hours and the synthesis time (first synthesis result) of the target product is 14 hours, the first synthesis result—the target synthesis result>1 hour, and thus, the processor 130 may calculate the second synthesis method.

When the processor 130 calculates the second synthesis method, the processor 130 may calculate new synthesis conditions for the second synthesis method by receiving the first synthesizing result as feedback. In an embodiment, the processor 130 may calculate the second synthesis method by changing at least one of the synthesis route and the synthesis conditions based on the first synthesis result. For example, based on the first synthesis result, the processor 130 may increase the synthesis temperature of the target product from 120° C. to 130° C. or may change a solvent from N,N-dimethylacetamide (DMAc) to N,N-dimethylformamide (DMF). The processor 130 may control the at least one device 110 based on the second synthesis method to prepare the target product.

The processor 130 may receive synthesis results as feedback until synthesis conditions are optimized. In some embodiments, the processor 130 may repeatedly calculate new synthesis conditions until a value obtained by subtracting a target synthesis result from the current synthesis result satisfies a preset condition. In addition, the processor 130 may store synthesis results in the memory 140.

As described above, according to the disclosure, the processor 130 calculates synthesis methods, and thus users are not involved in the calculation of synthesis methods. In addition, according to an example embodiment, a target product is prepared as the processor 130 controls the at least one device 110, and as such, no user is involved when the at least one device 110 is controlled based on a calculated synthesis method. Therefore, the entire process for synthesizing a material may be automatically performed.

In addition, the processor 130 changes at least one of a synthesis route and synthesis conditions based on the previous synthesis result, and this feedback is repeatedly performed until a value obtained by subtracting a target synthesis result from the current synthesis result satisfies a preset condition, such that a target product may be optimally synthesized. Hereinafter, operations of the material synthesis apparatus 100 will be described with reference to FIGS. 2 and 3.

Figure 2:
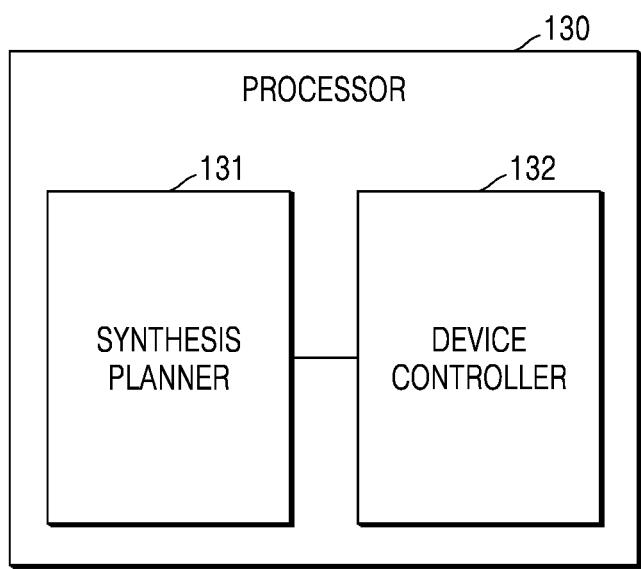
FIG. 2 is a block diagram illustrating a configuration of a processor according to an example embodiment.

FIG. 2 is a block diagram illustrating a configuration of the processor 130 according to an example embodiment.

The processor 130 may include a synthesis planner 131 and a device controller 132. The synthesis planner 131 may calculate a synthesis method for preparing a target product by using the synthesis prediction model stored in the memory 140. The device controller 132 may prepare a target product by controlling the at least one device 110 based on the calculated synthesis method.

Figure 3:
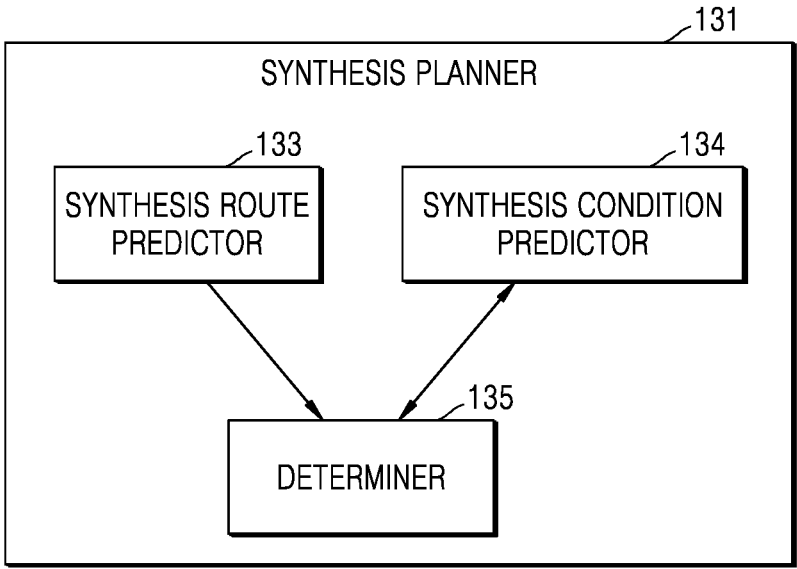
FIG. 3 is a block diagram illustrating a configuration of a synthesis planner according to an example embodiment.

FIG. 3 is a block diagram illustrating a configuration of the synthesis planner 131 according to an example embodiment.

The synthesis planner 131 may include a synthesis route predictor 133, a synthesis condition predictor 134, and a determiner 135. The synthesis route predictor 133 may predict a synthesis route for synthesizing a target product by using the pretrained synthesis prediction model, and the determiner 135 may determine the synthesis route. The synthesis condition predictor 134 may predict a combination of at least one synthesis condition for the determined synthesis route. The determiner 135 may predict results of synthesis for each combination of synthesis conditions, and may determine a synthesis method by determining a combination of synthesis conditions that are predicted to result in optimal synthesis results.

FIG. 4 is a diagram illustrating a method of controlling at least one device 430 by using the processor 130 according to an example embodiment. The processor 130 (for example, the processor 130 shown in FIGS. 1 to 3) may control the at least one device 430 according to control items 420 of synthesis operations.

In a transfer operation S411, the processor 130 may transmit commands about a destination and a transfer time of reagents to a storage device 431 and a carrier 432, thereby controlling the transfer of the reagents. The storage device 431 may put out the reagents, and the carrier 432 may transfer the reagents to a dispenser 433.

In an injection operation S412, the processor 130 may transmit commands about the injection amount, injection time, and injection method of the reagents to the dispenser 433, thereby controlling the injection of the reagents. The dispenser 433 may dispense the reagents and inject the reagents into a reaction vessel of a reactor 434.

In a reaction operation S413, the processor 130 may transmit commands about control of the temperature of the reaction vessel to the reactor 434, thereby controlling a reaction. The reactor 434 may heat or cool the reaction vessel to control the reaction.

In a collection operation S414, the processor 130 may transmit commands about the collection amount, collection time, and collection method of a sample to a collector 435, thereby controlling the collection of the sample. The collector 435 may collect the sample during or after the reaction and may transfer the sample to the analyzer 436.

In an analysis operation S415, the processor 130 may transmit commands about pretreatment and analysis methods to the analyzer 436, thereby analyzing the sample. The analyzer 436 may pretreat the sample and analyze the sample, and may transmit results of the analysis to the processor 130. The pretreatment may refer to a treatment which is performed on the sample before the analysis of the sample for accurate analysis of the sample. For example, the pretreatment may be precipitation, filtration, distillation, extraction, or the like, but is not limited thereto.

Figure 6:
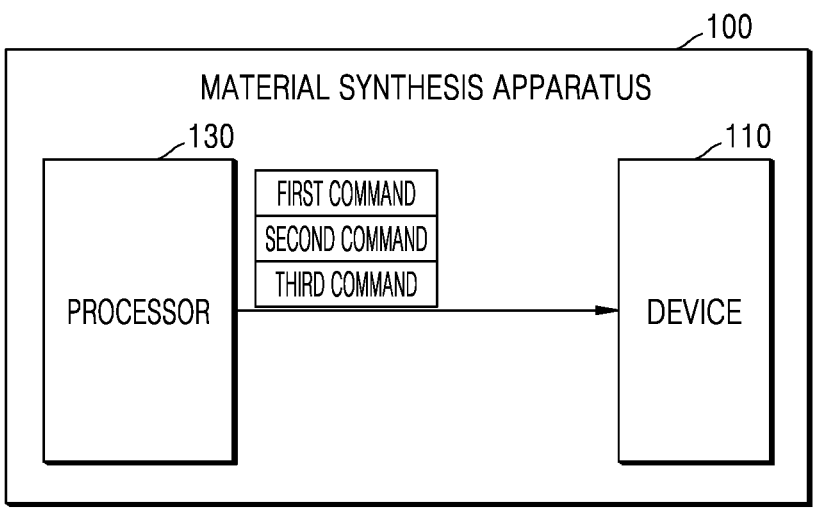

FIGS. 5 and 6 are diagrams illustrating a method of transmitting commands to the at least one device 110 from the processor 130 according to an example embodiment.

Referring to FIG. 5, the processor 130 may sequentially transmit commands for synthesizing a target product to the at least one device 110. The commands may be transmitted to the at least one device 110 at different times. When the commands are transmitted to the at least one device 110 at different times, the at least one device 110 may perform the commands in the order in which the command are transmitted to the at least one device 110.

For example, the processor 130 may transmit a first command to the at least one device 110 at a first time. In addition, the processor 130 may transmit a second command to the at least one device 110 at a second time later than the first time. In addition, the processor 130 may transmit a third command to the at least one device 110 at a third time later than the second time. After the at least one device 110 performs the first command, which is first received, the at least one device 110 may perform the second command and then finally the third command.

For example, when the at least one device 110 is the dispenser 433, the first command transmitted to the dispenser 433 may be "Inject 100 g of a reactant A into the reaction vessel", the second command transmitted to the dispenser 433 may be "Inject 50 g of a reactant B into the reaction vessel", and the third command transmitted to the dispenser 433 may be "Inject 500 ml of a solvent C into the reaction vessel". When receiving the first command, the dispenser 433 may inject 100 g of the reactant A into the reaction vessel. In addition, the dispenser 433 may inject 50 g of the reactant B into the reaction vessel when receiving the second command. In addition, the dispenser 433 may inject 500 ml of the solvent C into the reaction vessel when receiving the third command.

Referring to FIG. 6, the processor 130 may simultaneously transmit commands for synthesizing a target product to the at least one device 110. A combination of commands may be transmitted to the at least one device 110. When a combination of commands is transmitted to the at least one device 110, the at least one device 110 may sequentially perform the commands included in the combination of commands.

When it is required to sequentially perform a first command, a second command, and a third command to synthesize the target product, the processor 130 may transmit a combination of the first command, the second command, and the third command to the at least one device 110. The at least one device 110 may include a scheduler, and may sequentially perform the first command, the second command, and the third command by using the scheduler.

For example, when the at least one device 110 is the dispenser 433, the dispenser 433 may receive a combination of commands including first to third commands. In this case, the first command may be "Inject 100 g of a reactant A into the reaction vessel", the second command may be "Inject 50 g of a reactant B into the reaction vessel", and the third command may be "Inject 500 ml of a solvent C into the reaction vessel." The scheduler may determine the order of commands included in the combination of commands. The scheduler may schedule the commands in the order of the first command, the second command, and the third command. The dispenser 433 may perform the commands using the scheduler. First, according to a schedule determined by the scheduler, the dispenser 433 may inject 100 g of the reactant A into the reaction vessel, and thereafter, the dispenser 433 may inject 50 g of the reactant B into the reaction vessel and then finally 500 ml of the solvent C into the reaction vessel.

When a combination of commands is transmitted to the at least one device 110, a device for transmitting and receiving commands does not need to be operated during the entire process of synthesis, and thus, the power consumption of the material synthesis apparatus 100 may be reduced. Furthermore, in the method of transmitting a combination of commands to the at least one device 110, all the commands may be transmitted or may not be transmitted, thereby preventing situations in which commands may not be sequentially performed because some of the commands are not transmitted.

Figure 7:
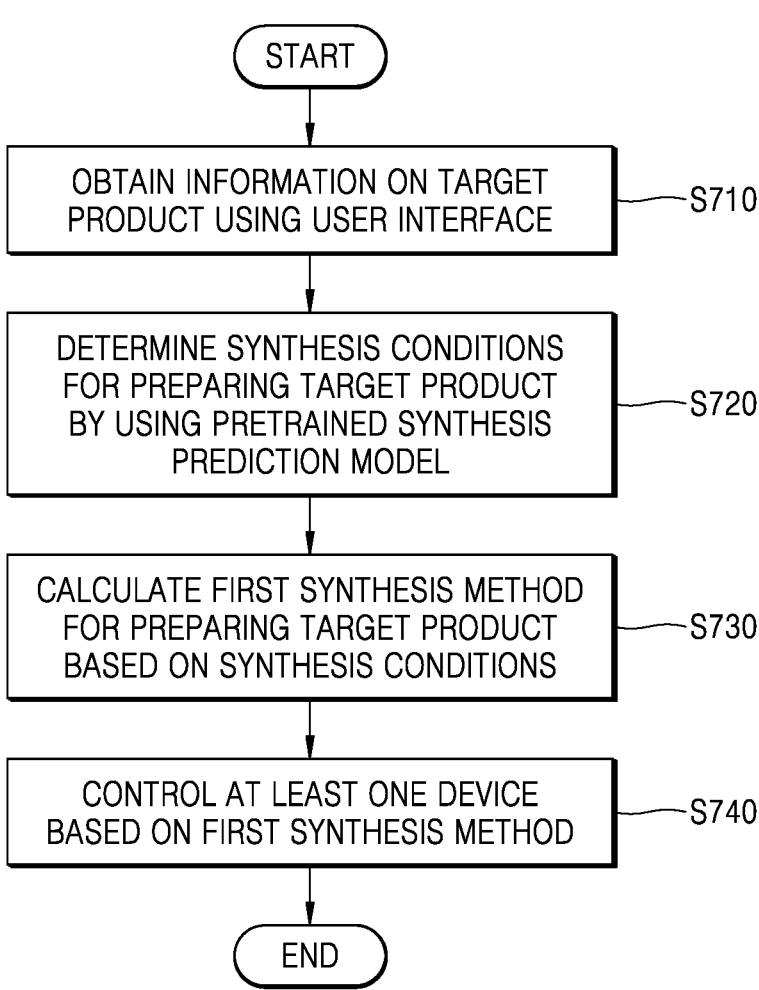
FIG. 7 is a flowchart illustrating a method of operating a material synthesis apparatus according to an example embodiment.

FIG. 7 is a flowchart illustrating a method of operating a material synthesis apparatus according to an example embodiment.

Referring to FIG. 7, the method of operating a material synthesis apparatus may include operations which the material synthesis apparatus 100 illustrated in FIG. 1 may perform. According to an example embodiment, the material synthesis apparatus may perform the operations in a time-series manner. Therefore, it will be understood that the descriptions given with reference to FIGS. 1 to 6 are also applicable to the method of operating a material synthesis apparatus shown in FIG. 7 even though descriptions are omitted below. However, the disclosure is not limited to the illustrated operations in FIG. 7.

In operation S710, the material synthesis apparatus 100 may obtain information on a target product using the user interface 120. According to an example embodiment, after obtaining the information on the target product, the material synthesis apparatus 100 may further obtain a target synthesis result regarding the target product by using the user interface 120.

The information on the target product may include structure information on the target product. The target synthesis result may refer to an arbitrary quantitative value of an index related to the synthesis of the target product. Examples of the target synthesis result may include a target synthesis yield, a target synthesis amount, a target synthesis time, or the like, but are not limited thereto.

In operation S720, the processor 130 may determine synthesis conditions for preparing the target product using a pretrained synthesis prediction model.

The processor 130 may determine a synthesis route for synthesizing the target product by using the pretrained synthesis prediction model, and may determine synthesis conditions for the determined synthesis route.

The synthesis prediction model may be generated by the processor 130 based on a database such as Reaxys or SciFinder. For example, the processor 130 may generate the synthesis prediction model using a DNN, an RNN, a CVAE, or the like. The synthesis route may refer to a chemical reaction through which the target product is prepared from reactants. A plurality of synthesis routes may exist depending on structure information on the reactants and the structure information on the target product. The synthesis conditions may refer to various conditions which are set to proceed with the chemical reaction for preparing the target product from the reactants, and at least one synthesis condition may be set for each synthesis route.

In operation S730, the processor 130 may calculate a first synthesis method for preparing the target product based on the synthesis conditions.

The processor 130 may determine the synthesis route for synthesizing the target product by using the pretrained synthesis prediction model. The processor 130 may determine synthesis conditions for the determined synthesis route by using the pretrained synthesis prediction model, and may calculate the first synthesis method based on the determined synthesis route and the synthesis conditions.

In operation S740, the processor 130 may control the at least one device 110 based on the first synthesis method.

As the processor 130 controls the at least one device 110, the target product may be prepared according to the first synthesis method.

Figure 8:
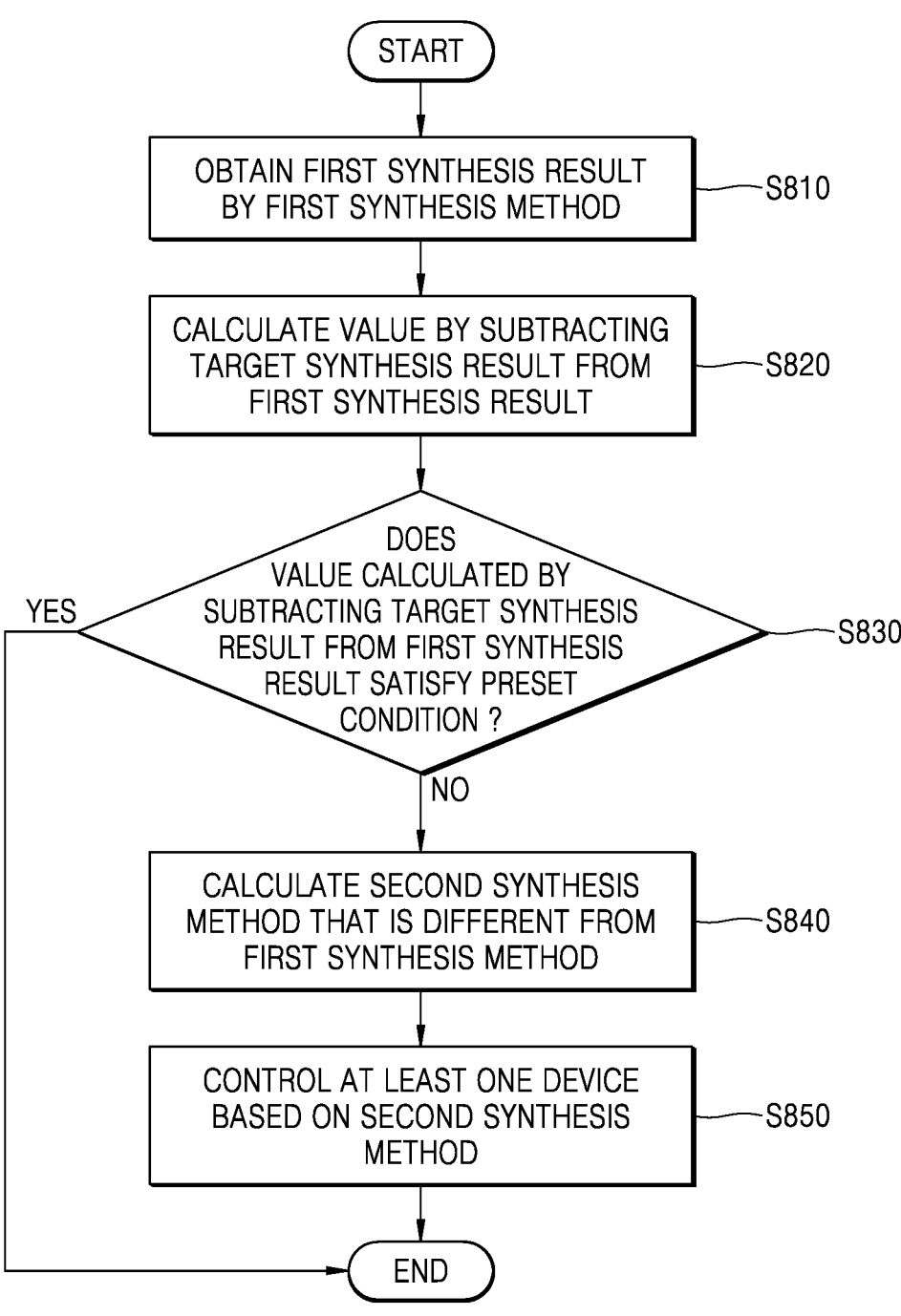
FIG. 8 is a flowchart illustrating a feedback method for the material synthesis apparatus according to an example embodiment.

FIG. 8 is a flowchart illustrating a feedback method for the material synthesis apparatus 100 according to an example embodiment.

Referring to FIG. 8, in operation S810, the processor 130 may obtain a first synthesis result according to a first synthesis method.

The first synthesis result may refer to an arbitrary quantitative value of an index related to the synthesis of a target product prepared using the first synthesis method. For example, examples of the first synthesis result may include, but are not limited to, the synthesis yield, synthesis amount, and synthesis time of the target product prepared using the first synthesis method.

Based on results of comparison between a target synthesis result and the first synthesis result, the processor 130 may determine whether to calculate a second synthesis method which is different from the first synthesis method.

In operation S820, the processor 130 may calculate a value by subtracting the target synthesis result from the first synthesis result.

The target synthesis result may include a quantitative index related to the yield, amount, or time of synthesis. When the quantitative index of the target synthesis result is the yield of synthesis, a target synthesis yield is 80%, and the synthesis yield (first synthesis result) of the target product is 85%, the value obtained by subtracting the target synthesis result from the first synthesis result may be "+5%." When the target synthesis yield is 80%, and the synthesis yield (first synthesis result) of the target product is 75%, the value obtained by subtracting the target synthesis result from the first synthesis result is "−5%."

In operation S830, the processor 130 may determine whether the value obtained by subtracting the target synthesis result from the first synthesis result satisfies a specific condition. According to an example embodiment, the specific condition may be predetermined.

In operation S840, when the value obtained by subtracting the target synthesis result from the first synthesis result does not satisfy the preset condition, the processor 130 may calculate a second synthesis method which is different from the first synthesis method.

For example, when the target synthesis result is the yield of synthesis, the preset condition may be set to be "0% or more". In this case, when the value obtained by subtracting the target synthesis result from the first synthesis result is "−5%," the preset condition is not satisfied, and thus, the processor 130 may calculate the second synthesis method which is different from the first synthesis method. The processor 130 may calculate the second synthesis method which is different from the first synthesis method by increasing the synthesis temperature of the target product or changing a solvent in the first synthesis method, but is not limited thereto.

In operation S850, the processor 130 may control the at least one device 110 based on the second synthesis method.

The processor 130 may calculate the second synthesis method by changing at least one of a synthesis route and synthesis conditions based on the first synthesis result. The target product may be prepared according to the calculated second synthesis method by controlling the at least one device 110 based on the calculated second synthesis method.

The processor 130 may receive synthesis results as feedback until synthesis conditions are optimized. In some embodiments, the processor 130 may repeatedly calculate new synthesis conditions until the value obtained by subtracting the target synthesis result from the current synthesis result satisfies the preset condition.

Figure 9:
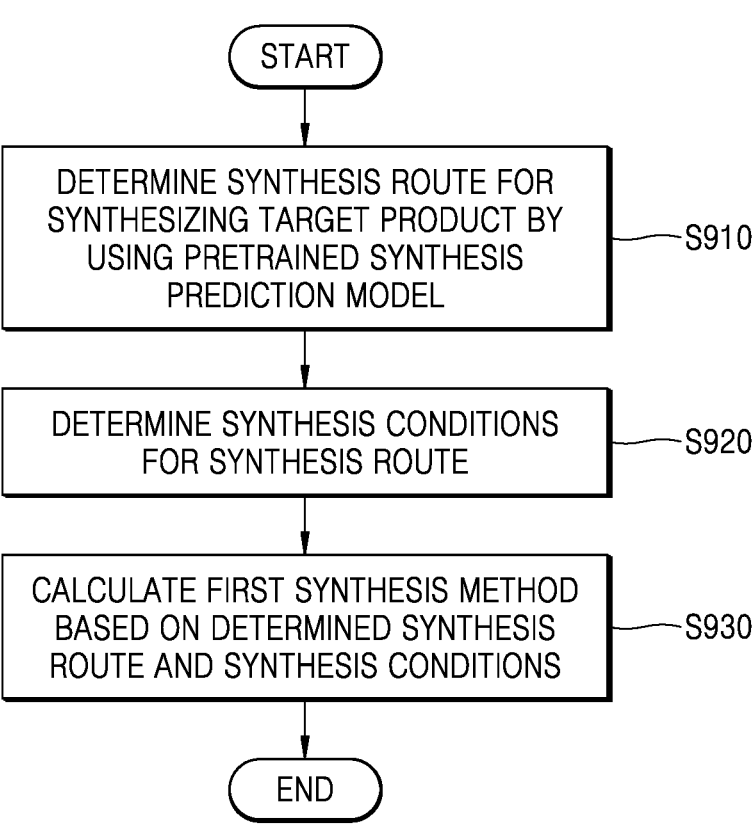
FIG. 9 is a flowchart illustrating a method of calculating a synthesis method according to an example embodiment.

FIG. 9 is a flowchart illustrating a method of calculating a synthesis method according to an example embodiment.

Referring to FIG. 9, in operation S910, the processor 130 may determine a synthesis route for synthesizing a target product using a pretrained synthesis prediction model.

The synthesis route predictor 133 of the processor 130 may predict a synthesis route for synthesizing the target product by using the pretrained synthesis prediction model, and the determiner 135 of the processor 130 may determine the synthesis route.

In operation S920, the processor 130 may determine synthesis conditions for the synthesis route.

The synthesis condition predictor 134 of the processor 130 may predict a combination of at least one synthesis condition for the determined synthesis route by using the pretrained synthesis prediction model. The determiner 135 of the processor 130 may predict a synthesis result for each combination of synthesis conditions, and may determine a combination of synthesis conditions that are predicted to result in an optimal synthesis result.

In operation S930, the processor 130 may calculate a first synthesis method based on the determined synthesis route and the determined synthesis conditions.

Figure 10:
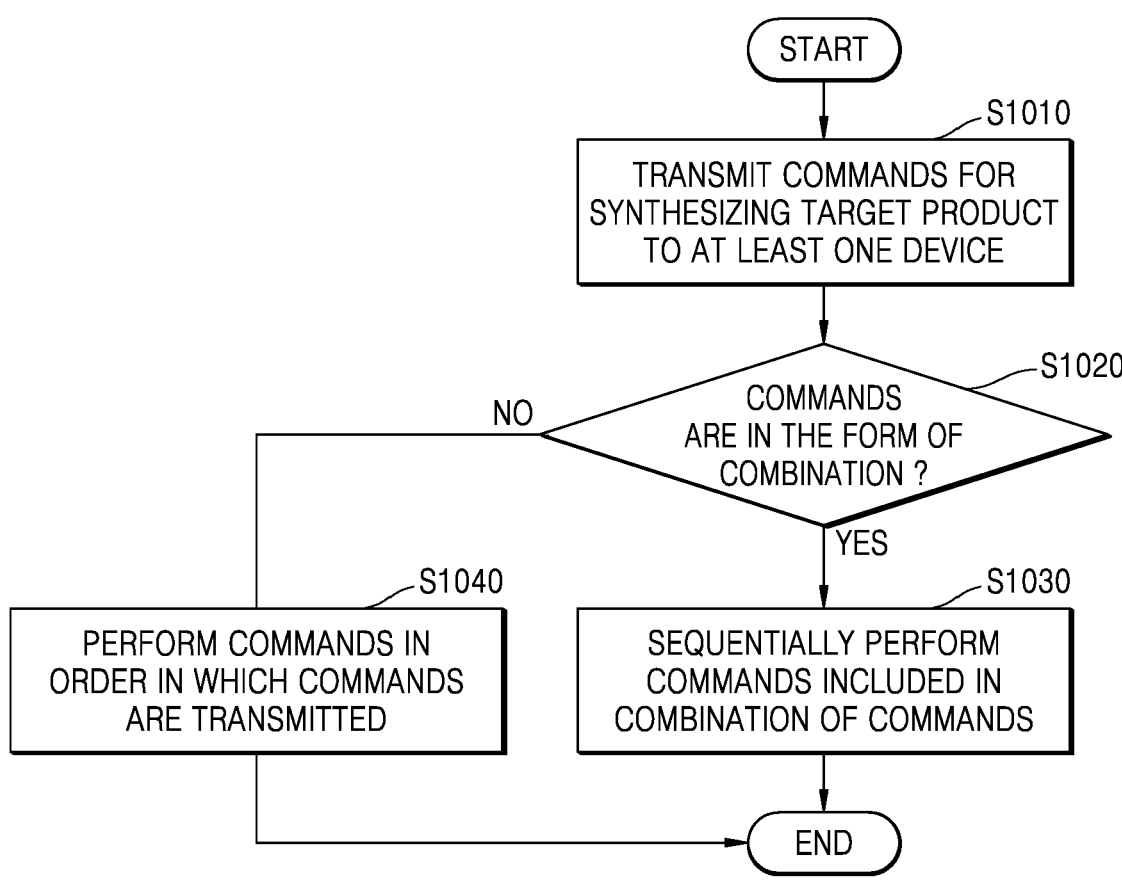
FIG. 10 is a flowchart illustrating a method of controlling the at least one device according to an example embodiment.

FIG. 10 is a flowchart illustrating a method of controlling the at least one device 110 according to an example embodiment.

Referring to FIG. 10, in operation S1010, the processor 130 may transmit commands for synthesizing a target product to the at least one device 110.

The processor 130 may transmit the commands to the at least one device 110 sequentially or simultaneously. When the processor 130 transmits the commands to the at least one device 110 at the same time, the commands transmitted to the at least one device 110 may be in the form of a combination.

In operation S1020, the at least one device 110 may determine whether the commands received from the processor 130 are in the form of a combination.

In operation S1030, when the commands received from the processor 130 are in the form of a combination, the at least one device 110 may sequentially perform the commands included in the combination of commands. The at least one device 110 may include a scheduler, and may sequentially perform the commands included in the combination of commands by using the scheduler.

When a combination of commands is transmitted to the at least one device 110, a device for transmitting and receiving commands does not need to be operated during the entire process of synthesis, and thus, the power consumption of the material synthesis apparatus 100 may be reduced. Furthermore, in the method of transmitting a combination of commands to the at least one device 110, all the commands may be transmitted or may not be transmitted, thereby preventing situations in which commands may not be sequentially performed because some of the commands are not transmitted.

In operation S1040, when the commands transmitted from the processor 130 are not in the form of a combination, the at least one device 110 may perform the commands in the order in which the commands are transmitted.

Figure 11:
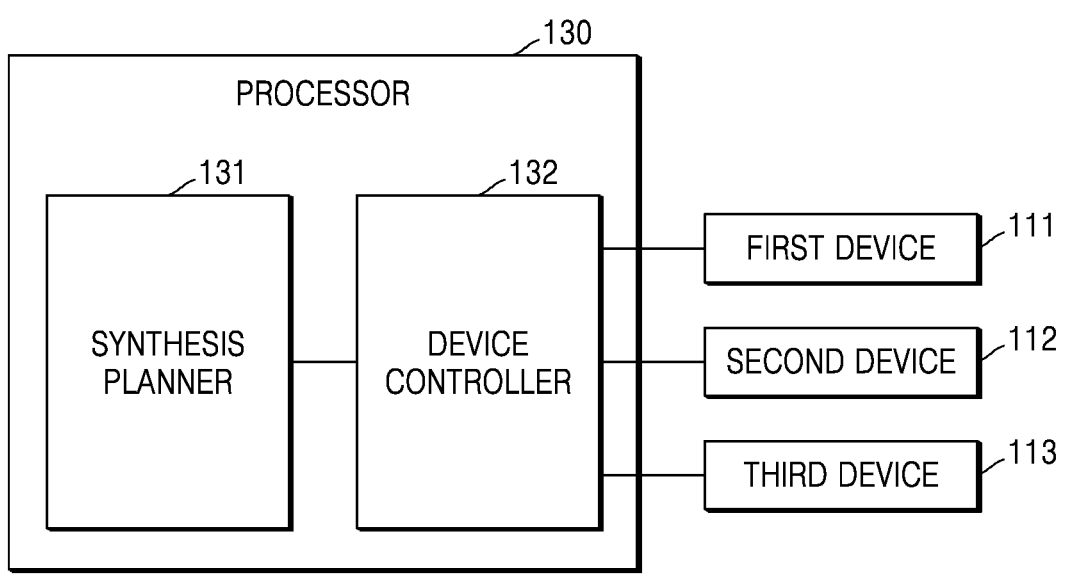
FIG. 11 is a block diagram illustrating the processor which controls a plurality of devices according to an example embodiment.

FIG. 11 is a block diagram illustrating the processor 130 which controls a plurality of devices according to an embodiment.

Referring to FIG. 11, the material synthesis apparatus 100 may include the processor 130, a first device 111, a second device 112, and a third device 113. The processor 130 may include a synthesis planner 131 and a device controller 132. According to different example embodiment, different number of devices may be provided.

The processor 130 may control the first device 111, the second device 112, and the third device 113 sequentially or simultaneously. The processor 130 may control the first device 111, the second device 112, and the third device 113 by sequentially or simultaneously transmitting commands or a combination of commands for synthesizing a target product to the first device 111, the second device 112, and the third device 113.

The processor 130 may sequentially transmit commands to the first device 111, the second device 112, and the third device 113. The commands may be transmitted to the first device 111, the second device 112, and the third device 113 at different times. When commands are transmitted to the first device 111, the second device 112, and the third device 113 at different times, the first device 111, the second device 112, and the third device 113 may perform the commands in the order in which the commands are transmitted thereto.

The processor 130 may transmit combinations of commands for synthesizing a target product to the first device 111, the second device 112, and the third device 113, respectively. The combinations of commands may include a first command combination, a second command combination, and a third command combination. When the first command combination is transmitted to the first device 111, the second command combination is transmitted to the second device 112, and the third command combination is transmitted to the third device 113, each of the first device 111, the second device 112, and the third device 113 may sequentially perform the commands included in the command combination transmitted thereto.

The example embodiments may be written as computer programs and may be implemented in general-use digital computers that execute the programs using non-transitory computer-readable recording media. The information used in the aforementioned example embodiments may be recorded in computer-readable recording media through various members. Examples of the non-transitory computer-readable recording media include magnetic storage media (e.g., read-only memory (ROM), floppy disks, and hard disks) and optical reading media (e.g., CD-ROMs and digital video disks (DVDs)).

It should be understood that example embodiments described herein should be considered in a descriptive sense only and not for purposes of limitation. Descriptions of features or aspects within each embodiment should typically be considered as available for other similar features or aspects in other example embodiments. While one or more example embodiments have been described with reference to the figures, it will be understood by those of ordinary skill in the art that various changes in form and details may be made therein without departing from the spirit and scope as defined by the following claims.

What is claimed is:

1. A material synthesis apparatus comprising:
at least one device configured to synthesize a material;
a user interface configured to obtain information on a target product;
memory storing a pretrained synthesis prediction model; and
a processor configured to:
obtain pretrained synthesis prediction model from the memory;
determine, using the pretrained synthesis prediction model, a synthesis route for synthesizing the target product;
determine, using the pretrained synthesis prediction model, one or more synthesis conditions for preparing the target product based on the synthesis route;
determine a first synthesis method for preparing the target product based on the one or more synthesis conditions; and
automatically control one or more first operations of the at least one device to synthesize the material based on the first synthesis method,
wherein the user interface is further configured to obtain a target synthesis result regarding the target product,
wherein the processor is further configured to:
obtain a first synthesis result related to the synthesized material from the at least one device based on the first synthesis method;
determine, based on a result of a comparison between the target synthesis result and the first synthesis result, whether to determine a second synthesis method which is different from the first synthesis method; and
automatically control one or more second operations of the at least one device based on the second synthesis method based on the determination to determine the second synthesis method,
wherein the target synthesis result comprises at least one of a target synthesis yield, a target synthesis amount, or a target synthesis time of the target product.

2. The material synthesis apparatus of claim 1, wherein the processor is further configured to:
calculate a value by subtracting the target synthesis result from the first synthesis result, and
determine the second synthesis method based on whether the value satisfies a specific condition.

3. The material synthesis apparatus of claim 1, further comprising wherein the processor is further configured to:
determine the second synthesis method by changing, based on the first synthesis result, at least one of the determined synthesis route or the determined one or more synthesis conditions.

4. The material synthesis apparatus of claim 1, wherein the information on the target product comprises structure information on the target product.

5. The material synthesis apparatus of claim 1, wherein the processor is further configured to transmit a combination of commands for synthesizing the target product to the at least one device.

6. The material synthesis apparatus of claim 5, wherein the at least one device is further configured to sequentially perform the commands included in the combination of commands.

7. The material synthesis apparatus of claim 1, further comprising a communication interface configured to receive a target synthesis result regarding the target product from an external device.

* * * * *